US012734675B2

(12) United States Patent
Zeng et al.

(10) Patent No.: US 12,734,675 B2
(45) Date of Patent: Sep. 15, 2026

(54) AUXILIARY SUPPORT METHOD BASED ON VARIABLE STIFFNESS SUPERNUMERARY ROBOTIC LIMBS

(71) Applicant: SOUTHEAST UNIVERSITY, Nanjing (CN)

(72) Inventors: Hong Zeng, Nanjing (CN); Huayu Zhang, Nanjing (CN); Jianxi Zhang, Nanjing (CN); Aiguo Song, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 876 days.

(21) Appl. No.: 18/022,748

(22) PCT Filed: Jul. 25, 2022

(86) PCT No.: PCT/CN2022/107556
§ 371 (c)(1),
(2) Date: Sep. 14, 2023

(87) PCT Pub. No.: WO2023/168887
PCT Pub. Date: Sep. 14, 2023

(65) Prior Publication Data

US 2024/0033899 A1 Feb. 1, 2024

(30) Foreign Application Priority Data

Mar. 9, 2022 (CN) ........................ 202210231857.9

(51) Int. Cl.
*A61F 2/72* (2006.01)
*A61B 5/00* (2006.01)
(Continued)

(52) U.S. Cl.
CPC ............ *B25J 9/0006* (2013.01); *A61B 5/397* (2021.01); *A61B 5/4851* (2013.01);
(Continued)

(58) Field of Classification Search
None
See application file for complete search history.

(56) References Cited

U.S. PATENT DOCUMENTS

2017/0348851 A1 12/2017 Artemiadis et al.
2020/0170547 A1 6/2020 Bai et al.

FOREIGN PATENT DOCUMENTS

CN 106109174 A 11/2016
CN 110355761 A 10/2019
(Continued)

OTHER PUBLICATIONS

The National Bureau of Statistics, The Report on Monitoring Survey of Migrant Workers in 2020, 2021.

*Primary Examiner* — David H Willse
(74) *Attorney, Agent, or Firm* — Bayramoglu Law Offices LLC

(57) ABSTRACT

An auxiliary support method based on variable stiffness supernumerary robotic limbs includes: obtaining data from a surface electromyography sensor and an inertial sensor; processing the data from the inertial sensor to determine whether a wearer has an operation intention; preprocessing the data from the surface electromyography sensor through full-wave rectification, low-pass filtering and normalization; using preprocessed surface electromyography to estimate a reference stiffness of an arm of the wearer; and mapping the reference stiffness of the arm to an impedance control model of the supernumerary robotic limbs. In the method, man-machine cooperation between human and the supernumerary robotic limbs in a task of overhead support is achieved by coordinating a stiffness of the human arm and a stiffness of the supernumerary robotic limbs, thereby reducing input of personnel in the task; and when the stiffness of the arm of the wearer decreases, the stiffness of the supernumerary robotic limbs increases.

6 Claims, 1 Drawing Sheet

(51) Int. Cl.

| | |
|---|---|
| ***A61B 5/397*** | (2021.01) |
| ***A61F 2/54*** | (2006.01) |
| ***A61F 2/70*** | (2006.01) |
| ***A61F 5/01*** | (2006.01) |
| ***B25J 9/00*** | (2006.01) |
| ***G16H 40/63*** | (2018.01) |
| *A61F 2/76* | (2006.01) |

(52) U.S. Cl.

CPC .............. *A61B 5/6812* (2013.01); *A61F 2/54* (2013.01); *A61F 2/72* (2013.01); *G16H 40/63* (2018.01); *A61F 2002/704* (2013.01); *A61F 2002/7625* (2013.01); *A61F 2005/0155* (2013.01)

(56) References Cited

FOREIGN PATENT DOCUMENTS

| | | | | | |
|---|---|---|---|---|---|
| CN | 110900638 A | | 3/2020 | | |
| CN | 111309152 A | | 6/2020 | | |
| CN | 111897415 A | | 11/2020 | | |
| KR | 10-2017-0030139 A | * | 3/2017 | .............. | B25J 13/08 |

* cited by examiner

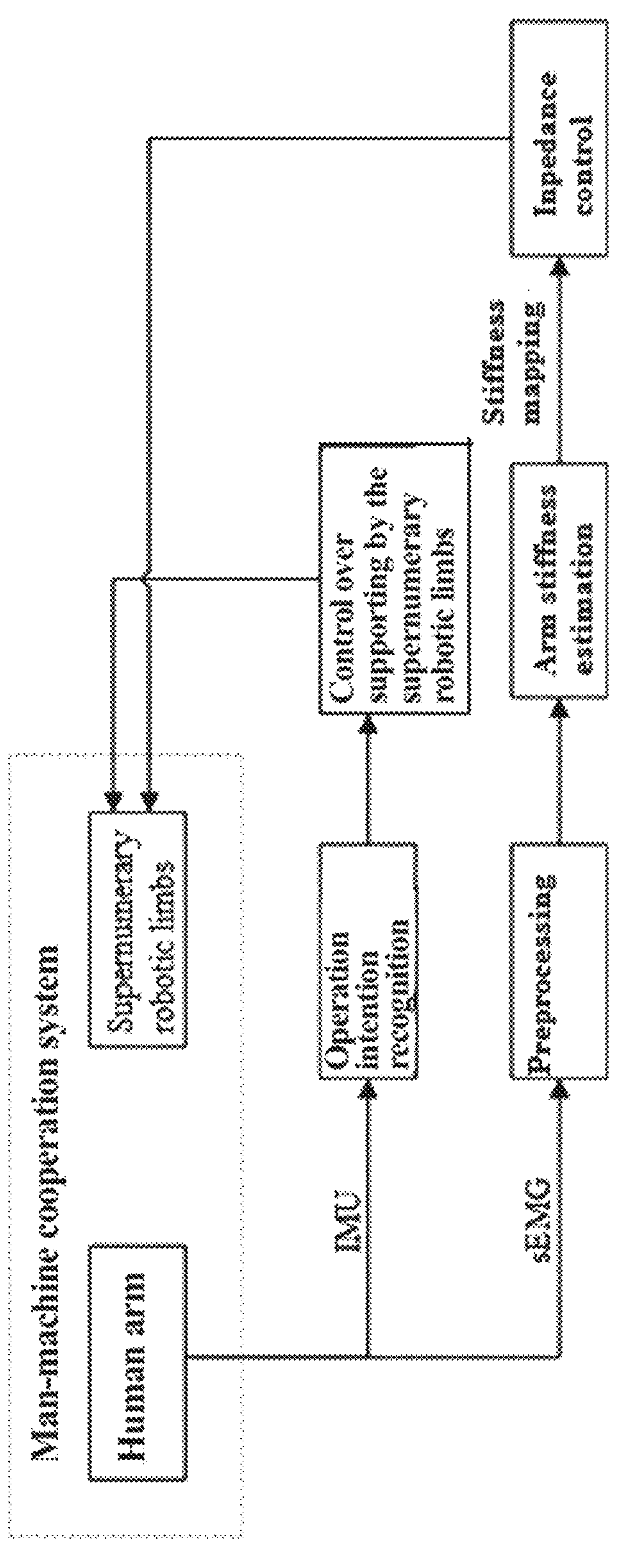
Man-machine cooperation system
Human arm
Supernumerary robotic limbs
IMU
sEMG
Operation intention recognition
Preprocessing
Control over supporting by the supernumerary robotic limbs
Arm stiffness estimation
Stiffness mapping
Inpedance control

AUXILIARY SUPPORT METHOD BASED ON VARIABLE STIFFNESS SUPERNUMERARY ROBOTIC LIMBS

This application is the national phase entry of International Application No. PCT/CN2022/107556, filed on Jul. 25, 2022, which is based upon and claims priority to Chinese Patent Application No. 202210231857.9, filed on Mar. 9, 2022, the entire contents of which are incorporated herein by reference.

TECHNICAL FIELD

The present disclosure belongs to the field of wearable robots, and in particular relates to an auxiliary support method based on variable stiffness supernumerary robotic limbs.

BACKGROUND

Rapid development of the aging population and changing of working concepts of people gradually highlight labor shortage. According to the Report on Monitoring Survey of Migrant Workers in 2020 released by the National Bureau of Statistics, in 2020, the total number of migrant workers in China decreased by 5.17 million, or 1.8% compared with that in last year, and the proportion of migrant workers 50 years old or older was 26.4% increasing by 1.8% compared with that in last year. So, the labor shortage and working condition improvement become great challenges faced by China and even the world during development. With the progress of robot technology, and full application of robots to lot manufacturing, large-scale application of the robots has become an important means to solve the labor shortage. Due to the working features of a batch manufacturing scene, the robots are highly specialized in work and closed in technological process, and can effectively improve efficiency in a standardized and modular working environment. However, in the case of an operation task featuring a large number of operation processes, high work intensity and high flexibility requirements, such as overhead assembly and support, it is difficult for large-scale mechanical apparatuses to assist in work on account of limitation of operation environment. In this case, simultaneous working of two workers is required. Besides, in the task of overhead assembly and support, the workers have to lift workpieces and components overhead and fix them on a ceiling or wall, during which, the workers can be injured after excessive and repetitive movement. Supernumerary robotic limbs, a novel wearable auxiliary operation robot, can be used as extra limbs to cooperate with people for performing operation tasks that cannot be completed by two hands of a single person in life or industry.

At present, common supernumerary robotic limbs include artificial limbs and an exoskeleton robot. The artificial limbs can compensate for lack of motor skills of the human body, but cannot enlarge working space of a wearer. The exoskeleton robot fits the limbs of the wearer and provides assistance for the human body by means of drive devices at joints, but can restrict the limb movement of the wearer. The supernumerary robotic limbs provide the wearer with mechanical limbs that are independent of physical limbs, can be worn in various ways, will not affect joint activities of the wearer, and can enlarge workspace and improve work efficiency of the wearer. The supernumerary robotic limbs can assist the wearer in completing complex tasks which are limited in environment and require cooperation of more than one person. Their application can reduce input of workers, and reduce the working intensity and the risk of fatigue injury of the workers.

SUMMARY

In order to solve the problems above, the present disclosure discloses an auxiliary support method based on variable stiffness supernumerary robotic limbs. According to the method, man-machine cooperation between human and the supernumerary robotic limbs in a task of overhead support by coordinating a stiffness of a human arm and a stiffness of the supernumerary robotic limbs, thereby reducing input of personnel in the task; and when the stiffness of the arm of a wearer decreases, the stiffness of the supernumerary robotic limbs increases, and the supernumerary robotic limbs can generate greater supporting force when an operator is tired, facilitating reduction of work intensity and risk of fatigue injury of the wearer.

In order to achieve the above objective, the present invention provides the following technical solution:

An auxiliary support method based on variable stiffness supernumerary robotic limbs, comprising:

- step 1, obtaining in real time original output data from a surface electromyography sensor and an inertial sensor placed on an arm of a wearer;
- step 2, processing data obtained from the inertial sensor to determine whether a human body has an operation intention, and assisting, under the condition that the human body has the operation intention, the human body in supporting an object to a required position by the supernumerary robotic limbs;
- step 3, preprocessing, after the object is in a supported state, original surface electromyography (sEMG) data through full-wave rectification, low-pass filtering and normalization;
- step 4, using preprocessed sEMG data to estimate a reference stiffness of the arm; and
- step 5, mapping the reference stiffness of the human arm to an impedance control model of the supernumerary robotic limbs.

Further, the original output data in step 1 are automatically read from the surface electromyography sensor and the inertial sensor in real time by a program, the surface electromyography sensor being placed at a position of an antagonistic muscle pair of biceps brachii and triceps brachii, and the inertial sensor being placed at a wrist of the human arm.

Further, signals provided by the inertial sensor in step 2 comprise a pitch angle, a yaw angle and a roll angle, and the pitch angle is selected as a feature of recognizing the operation intention through a specific computation method as follows:

$$\begin{cases} T=1, |\alpha-60^\circ| \le 10 \\ T=0, |\alpha-60^\circ| > 10 \end{cases}$$

wherein α represents a pitch angle at a current moment, T=1 indicates that there is an operation intention and T=0 indicates that there is no operation intention.

Further, a preprocessing method in step 3 comprises performing full-wave rectification on the original sEMG, all processed sEMG is non-negative, and a processing method is as follows:

$$P_1(i) = |EMG_{raw}(i)|$$

wherein i represents a sequence number of a sampling point, $EMG_{raw}(i)$ represents an amplitude of original sEMG at an $i^{th}$ sampling point, and $P_1(i)$ represents an amplitude of the sEMG at the $i^{th}$ sampling point after full-wave rectification;

low-pass filtering is performed on the sEMG subjected to full-wave rectification by a second-order Butterworth filter selected as a low-pass filter, processed sEMG has a noise envelope removed, and a processing method is as follows:

$$P_2(i) = LPF(P_1(i), f)$$

wherein $P_2(i)$ represents an amplitude of sEMG at the $i^{th}$ sampling point after low-pass filtering, LPF represents a signal amplitude, and f represents a cut-off frequency of the low-pass filter; and normalization is performed based on maximal voluntary contraction on an sEMG envelope subjected to low-pass filtering, and a processing method as follows:

$$P_3(i) = \frac{P_2(i)}{M}$$

wherein $P_3(i)$ represents an amplitude of the sEMG at the $i^{th}$ sampling point after normalization, and M represents an amplitude of the sEMG upon maximum contraction of a muscle.

Further, a method for computing the reference stiffness in step 4 comprises: computing muscle activations of an agonistic muscle pair and an antagonistic muscle pair through a computation method as follows:

$$a(i) = \frac{e^{AP_3(i)} - 1}{e^A - 1}$$

wherein a(i) represents a muscle activation, and A represents a nonlinear reference with a value range of (−3, 0);

after the muscle activations of the agonistic muscle and the antagonistic muscle are computed, the reference stiffness of the human arm can be represented with a smaller muscle activation of the agonistic muscle and the antagonistic muscle, and a computation method is as follows:

$$K_{ref} = \min(1, a_{agonist}, a_{antagonist})$$

wherein $K_{ref}$ represents a reference stiffness of the arm, and $a_{agonist}$ and $a_{antagonist}$ represent a muscle activation of the agonistic muscle and a muscle activation of the antagonistic muscle respectively.

Further, the impedance control model in step 5 is represented by a formula as follows:

$$M_d(\ddot{X} - \ddot{X}_d) + B_d(\dot{X} - \dot{X}_d) + K_d(X - X_d) = F_{ext}$$

wherein $M_d$, $B_d$ and $K_d$ represent an expected inertia matrix, an expected damping matrix and an expected stiffness matrix respectively, X, $\dot{X}$ and $\ddot{X}$ represents an actual displacement, an actual speed and actual acceleration, $X_d$, $\dot{X}_d$ and $\ddot{X}_d$ represent expected displacement, an expected speed and expected acceleration, and $F_{ext}$ represents interaction force between tail ends of the supernumerary robotic limbs and environment.

Further, a method for mapping the stiffness in step 5 comprises: mapping the stiffness to the supernumerary robotic limbs, and adjusting a stiffness matrix of the supernumerary robotic limbs, and a computation method is as follows:

$$K_{map} = (K_{max} - K_{min})K_{ref} + K_{min}$$

wherein $K_{max}$ and $K_{min}$ represent a maximum stiffness and a minimum stiffness of the supernumerary robotic limbs respectively, and $K_{map}$ represents a mapped stiffness; and the stiffness matrix and a damping matrix of the supernumerary robotic limbs are obtained by stiffness mapping, and a computation method is as follows:

$$K_d = S_k(1 - K_{map})$$

$$B_d = 2\zeta\sqrt{k_d}$$

wherein $K_d$ and $B_d$ represent a stiffness matrix and a damping matrix of the supernumerary robotic limbs respectively, $\zeta$ represents a damping ratio, and $S_k$ represents a coefficient diagonal matrix.

The present disclosure has the following beneficial effects:

(1) According to the auxiliary support method based on variable stiffness supernumerary robotic limbs of the present disclosure, man-machine cooperation between human and the supernumerary robotic limbs in the task of overhead support is achieved by coordinating the stiffness of the human arm and the stiffness of the supernumerary robotic limbs, thereby reducing input of personnel in the task.

(2) According to the method, a pitch angle provided by an inertial sensor placed on a wrist of the wearer is used to directly and efficiently determine an operation intention, and therefore the wearer may well complete the task of cooperative support by controlling the supernumerary robotic limbs.

(3) According to the method, a reference stiffness is used to act on the supernumerary robotic limbs through stiffness mapping, such that when the stiffness of the arm of the wearer decreases, the stiffness of the supernumerary robotic limbs increases, and the supernumerary robotic limbs can generate greater supporting force when the wearer is tired, thereby facilitating reduction of work intensity and reduction of risk of fatigue injury to the wearer.

BRIEF DESCRIPTION OF THE DRAWINGS

FIGURE is an overall block flow diagram of the present disclosure.

DETAILED DESCRIPTION OF THE EMBODIMENTS

The present disclosure will be further illustrated below with reference to accompanying drawings and specific embodiments, and it should be understood that the following specific embodiments are merely used to describe the present disclosure and not limit the scope of the present disclosure.

According to an auxiliary support method based on variable stiffness supernumerary robotic limbs of the present disclosure, human body is required to be in a supporting state, the supernumerary robotic limbs and the human body cooperate to fix a workpiece to a ceiling. A variable stiffness is mainly reflected in a scene where a man-machine cooperation system is disturbed and upper limbs of the human body are exhausted.

As shown in FIGURE, an auxiliary support method based on variable stiffness supernumerary robotic limbs provided by an example of the present disclosure includes:

(1) Obtain Signals from an Inertial Sensor and Recognize an Operation Intention

In the example, the inertial sensor is placed on a wrist of an arm of a wearer, and signals provided by the inertial sensor include a pitch angle, a yaw angle and a roll angle, and the pitch angle is selected as a feature of recognizing the operation intention through a specific computation method as follows:

$$\begin{cases} T = 1, |\alpha - 60°| \le 10 \\ T = 0, |\alpha - 60°| > 10 \end{cases}$$

where α represents a pitch angle at a current moment, T=1 indicates that there is an operation intention and T=0 indicates that there is no operation intention.

(2) Obtain and Preprocess Surface Electromyography (sEMG)

Under control of a central nervous system, the surface electromyography is a kind of non-stationary weak signal that is superimposed on skin surface by an action potential sequence generated by a motor unit after damping layer by layer. Therefore, original sEMG needs to be preprocessed through full-wave rectification, low-pass filtering and normalization.

Full-wave rectification is performed on the original sEMG, where all processed sEMG is non-negative, a processing method is as follows:

$$P_1(i) = |EMG_{raw}(i)|$$

where i represents a sequence number of a sampling point, $EMG_{raw}(i)$ represents an amplitude of an original sEMG at an $i^{th}$ sampling point, and $P_1(i)$ represents an amplitude of the sEMG at the $i^{th}$ sampling point subjected to full-wave rectification.

In order to remove a noise envelope of the sEMG, a common method is to extract a root mean square feature and an exponential moving average of the sEMG. In this example, low-pass filtering is performed on the sEMG subjected to full-wave rectification by a second-order Butterworth filter selected as a low-pass filter, where under the condition that processed sEMG has a noise envelope removed, a processing method is as follows:

$$P_2(i) = LPF(P_1(i), f)$$

where $P_2(i)$ represents an amplitude of sEMG at the $i^{th}$ sampling point subjected to low-pass filtering, LPF represents a signal amplitude, and f represents a cut-off frequency of the low-pass filter.

Normalization based on maximal voluntary contraction is performed on an sEMG envelope subjected to low-pass filtering in a processing method as follows:

$$P_3(i) = \frac{P_2(i)}{M}$$

where $P_3(i)$ represents an amplitude of the sEMG at the $i^{th}$ sampling point subjected to normalization, and M represents an amplitude of the sEMG upon maximum contraction of a muscle.

(3) Estimate Human Body Stiffness

The stiffness of human arms may be changed by co-contraction of an antagonistic muscle pair. When human muscles are in motion, because there is a nonlinear relation between an sEMG signal envelope and a muscle activation, a computation method is as follows:

$$a(i) = \frac{e^{AP_3(i)} - 1}{e^A - 1}$$

where a(i) represents the muscle activation, and A represents a nonlinear reference with a value range of (−3, 0), when A is close to −3, there is a high exponential relation between the sEMG envelope and the muscle activation, and when A is close to 0, there is a linear relation between the sEMG envelope and the muscle activation.

After computing the muscle activation of the agonistic muscle and antagonistic muscle, the reference stiffness of the human arm is represented with a smaller muscle activation of the agonistic muscle and the antagonistic muscle in a computation method as follows:

$$K_{ref} = \min(1, a_{agonisc}, a_{antagonist})$$

where $K_{ref}$ represents a reference stiffness of the arm, and $a_{agonist}$ and $a_{antagonist}$ represent a muscle activation of the agonistic muscle and a muscle activation of the antagonistic muscle respectively. Because a supporting task involves coordinated movement of a plurality of joints and a plurality of groups of muscle groups, in this example, a pair of agonistic muscles and antagonistic muscles related to elbow flexion and extension, namely biceps brachii and triceps brachii, are selected.

(4) Perform Stiffness Mapping and Impedance Control

In order to achieve compliance control over the supernumerary robotic limbs, this example uses a spring-damping-mass model to equivalent interaction between a tail end of the supernumerary robotic limbs and environment, and uses an impedance control strategy to dynamically adjust a relation between a position of the supernumerary robotic limbs and interaction force. An impedance control model may be expressed as follows:

$$M_d(\ddot{X}-\ddot{X}_d)+B_d(\dot{X}-\dot{X}_d)+K_d(X-X_d)=F_{ext}$$

where $M_d$, $B_d$ and $K_d$ represent an expected inertia matrix, an expected damping matrix and an expected stiffness matrix respectively, X, $\dot{X}$ and $\ddot{X}$ represents an actual displacement, an actual speed and actual acceleration, $X_d$, $\dot{X}_d$ and $\ddot{X}_d$ represent expected displacement, an expected speed and expected acceleration, and $F_{ext}$ represents interaction force between the tail end of the supernumerary robotic limbs and the environment.

The stiffness is mapped to the supernumerary robotic limbs, and a stiffness matrix of the supernumerary robotic limbs is adjusted in a computation method as follows:

$$K_{map}=(K_{max}-K_{min})K_{ref}+K_{min}$$

where $K_{max}$ and $K_{min}$ represent a maximum stiffness and a minimum stiffness of the supernumerary robotic limbs respectively, and $K_{map}$ represents a mapped stiffness.

The stiffness matrix and a damping matrix of the supernumerary robotic limbs are obtained by stiffness mapping in a computation method as follows:

$$K_d=S_k(1-K_{map})$$
$$B_d=2\zeta\sqrt{k_d}$$

where $K_d$ and $B_d$ represent a stiffness matrix and a damping matrix of the supernumerary robotic limbs respectively, ζ represents the damping ratio, and $S_k$ represents a coefficient diagonal matrix.

It shall be noted that what is described above is merely about technical ideas of present disclosure, and shall be not regarded as limitation to the protection scope of the present disclosure. For those of ordinary skill in the art, several improvements and polishing can be made on the premise without deviating from a principle of the present disclosure, and these improvements and polishing shall fall within the protection scope of the claims of the present disclosure.

What is claimed is:

1. An auxiliary support method based on variable stiffness supernumerary robotic limbs, comprising:

step 1, obtaining in real time original output data from a surface electromyography sensor and an inertial sensor placed on an arm of a wearer;

step 2, processing data obtained from the inertial sensor to determine whether a human body has an operation intention, and assisting, under a condition that the human body has the operation intention, the human body in supporting an object to a required position by the supernumerary robotic limbs;

step 3, preprocessing, after the object is in a supported state, original surface electromyography (sEMG) data through full-wave rectification, low-pass filtering and normalization;

step 4, using preprocessed sEMG data to estimate a reference stiffness of the arm; and step 5, mapping the reference stiffness of the human arm to an impedance control model of the supernumerary robotic limbs;

signals provided by the inertial sensor in step 2 comprise a pitch angle, a yaw angle and a roll angle, and the pitch angle is selected as a feature of recognizing the operation intention through a specific computation method as follows:

$$\begin{cases} T=1, |\alpha-60°|\le 10 \\ T=0, |\alpha-60°|>10 \end{cases}$$

wherein α represents a pitch angle at a current moment, T=1 indicates that there is an operation intention and T=0 indicates that there is no operation intention.

2. The auxiliary support method based on variable stiffness supernumerary robotic limbs according to claim 1, wherein the original output data in step 1 are automatically read from the surface electromyography sensor and the inertial sensor in real time by a program, wherein the surface electromyography sensor is placed at a position of an antagonistic muscle pair of biceps brachii and triceps brachii, and the inertial sensor is placed at a wrist of the human arm.

3. The auxiliary support method based on variable stiffness supernumerary robotic limbs according to claim 1, wherein a preprocessing method in step 3 comprises performing full-wave rectification on the original sEMG, all processed sEMG is non-negative, and a processing method is as follows:

$$P_1(i)=|EMG_{row}(i)|$$

wherein i represents a sequence number of a sampling point, $EMG_{raw}(i)$ represents an amplitude of original sEMG at an $i^{th}$ sampling point, and represents an amplitude of the sEMG at the $i^{th}$ sampling point after full-wave rectification;

low-pass filtering is performed on the sEMG subjected to full-wave rectification by a second-order Butterworth filter selected as a low-pass filter, processed sEMG has a noise envelope removed, and a processing method is as follows;

$$P_2(i)=LPF(P_1(i), f)$$

wherein $P_2(i)$ represents an amplitude of sEMG at the $i^{th}$ sampling point after low-pass filtering, LPF represents a signal amplitude, and f represents a cut-off frequency of the low-pass filter; and normalization is performed based on maximal voluntary contraction on an sEMG envelope subjected to low-pass filtering, and a processing method as follows:

$$P_3(i)=\frac{P_2(i)}{M}$$

wherein $P_3(i)$ represents an amplitude of the sEMG at the $i^{th}$ sampling point after normalization, and M represents an amplitude of the sEMG upon maximum contraction of a muscle.

4. The auxiliary support method based on variable stiffness supernumerary robotic limbs according to claim 1, wherein a method for computing the reference stiffness in step 4 comprises: computing muscle activations of an agonistic muscle pair and an antagonistic muscle pair through a computation method as follows:

$$a(i) = \frac{e^{AP_3(i)} - 1}{e^A - 1}$$

wherein a(i) represents a muscle activation, and A represents a nonlinear reference with a value range of (−3, 0);

after the muscle activations of the agonistic muscle and the antagonistic muscle are computed, the reference stiffness of the human arm is represented with a smaller muscle activation of the agonistic muscle and the antagonistic muscle, and a computation method is as follows:

$$K_{ref} = \min(1, a_{agonist}, a_{antagonist})$$

wherein $K_{ref}$ represents a reference stiffness of the arm, and $a_{agonist}$ and $a_{antagonist}$ represent a muscle activation of the agonistic muscle and a muscle activation of the antagonistic muscle respectively.

5. The auxiliary support method based on variable stiffness supernumerary robotic limbs according to claim 1, wherein the impedance control model in step 5 is represented by a formula as follows:

$$M_d(\ddot{X} - \ddot{X}_d) + B_d(\dot{X} - \dot{X}_d) + K_d(X - X_d) = F_{ext}$$

wherein $M_d$, $B_d$ and $K_d$ represent an expected inertia matrix, an expected damping matrix and an expected stiffness matrix respectively, X, $\dot{X}$ and $\ddot{X}$ represents an actual displacement, an actual speed and an actual acceleration, $X_d$, $\dot{X}_d$ and $\ddot{X}_d$ represent an expected displacement, an expected speed and an expected acceleration, and $F_{ext}$ represents an interaction force between tail ends of the supernumerary robotic limbs and environment.

6. The auxiliary support method based on variable stiffness supernumerary robotic limbs according to claim 1, wherein a method for mapping the stiffness in step 5 comprises: mapping the stiffness to the supernumerary robotic limbs, and adjusting a stiffness matrix of the supernumerary robotic limbs, and a computation method is as follows:

$$K_{map} = (K_{max} - K_{min})K_{ref} + K_{min}$$

wherein $K_{max}$ and $K_{min}$ represent a maximum stiffness and a minimum stiffness of the supernumerary robotic limbs respectively, and $K_{map}$ represents a mapped stiffness; and the stiffness matrix and a damping matrix of the supernumerary robotic limbs are obtained by stiffness mapping, and a computation method is as follows:

$$K_d = S_k(1 - K_{map})$$

$$B_d = 2\zeta\sqrt{k_d}$$

wherein $K_d$ and $B_d$ represent the stiffness matrix and the damping matrix of the supernumerary robotic limbs respectively, ζ represents a damping ratio, and $S_k$ represents a coefficient diagonal matrix.

* * * * *